US012779065B2

(12) United States Patent
Payne et al.

(10) Patent No.: US 12,779,065 B2
(45) Date of Patent: Nov. 3, 2026

(54) UV DISINFECTION SYSTEM AND METHODS

(71) Applicant: Bard Access Systems, Inc., Salt Lake City, UT (US)

(72) Inventors: Dustin Payne, West Jordan, UT (US); Robin Scott Urry, Syracuse, UT (US); Debra K. Cloward, Springville, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 561 days.

(21) Appl. No.: 18/094,785

(22) Filed: Jan. 9, 2023

(65) Prior Publication Data

US 2024/0226351 A1 Jul. 11, 2024

(51) Int. Cl.

| | |
|---|---|
| ***A61L 2/10*** | (2026.01) |
| ***A61L 2/24*** | (2006.01) |
| *A61L 103/15* | (2026.01) |

(52) U.S. Cl.

CPC *A61L 2/10* (2013.01); *A61L 2/24* (2013.01); *A61L 2103/15* (2026.01); (Continued)

(58) Field of Classification Search

CPC .......... A61L 2/10; A61L 2/24; A61L 2202/11; A61L 2202/122; A61L 2202/14; A61L 2202/24

See application file for complete search history.

(56) References Cited

U.S. PATENT DOCUMENTS

| | | | |
|---|---|---|---|
| 5,225,172 A | 7/1993 | Meyler et al. | |
| 5,441,504 A | 8/1995 | Pohndorf et al. | |

(Continued)

FOREIGN PATENT DOCUMENTS

| | | | |
|---|---|---|---|
| CA | 2199384 C | 6/2006 | |
| CA | 3080966 A1 * | 11/2020 | .............. A61L 2/26 |

(Continued)

OTHER PUBLICATIONS

English translation of KR20110050077 (Year: 2011).*

(Continued)

*Primary Examiner* — Regina M Yoo

(74) *Attorney, Agent, or Firm* — Rutan & Tucker LLP

(57) ABSTRACT

A disinfection system can include a console and an operably connected disinfection unit. The console can have electronic circuitry including memory with executable instructions configured to cause the console to perform various processes when executed by one or more processors of the console. The various processes can include characterizing with medical-device characterization logic characteristics of at least an elongate portion of a medical device for establishing or maintaining vascular access in a patient. The various processes can also include determining with disinfection logic a disinfection profile for disinfecting at least the elongate portion of the medical device with ultraviolet ("UV") light. The disinfection unit can include a disinfection compartment suitably sized to enclose the medical device therein. A UV-light source disposed in the disinfection compartment can be for disinfecting at least the elongate portion of the medical device with the UV light in accordance with the disinfection profile.

8 Claims, 2 Drawing Sheets

Figure 1:
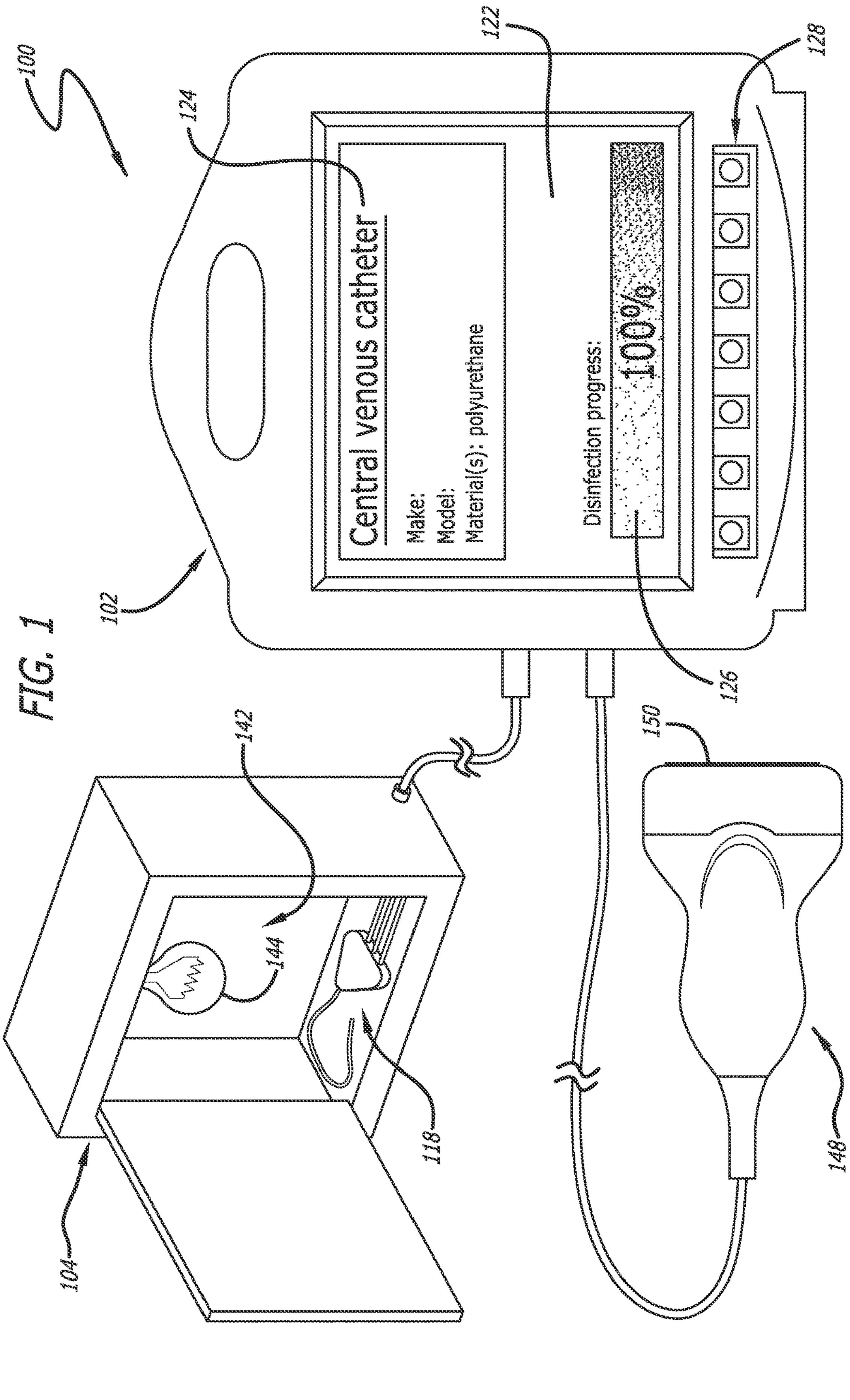

(52) U.S. Cl.
CPC ...... *A61L 2202/11* (2013.01); *A61L 2202/122* (2013.01); *A61L 2202/14* (2013.01)

(56) References Cited

U.S. PATENT DOCUMENTS

| | | | |
|---|---|---|---|
| 6,811,563 | B2 | 11/2004 | Savage, Jr. et al. |
| 6,908,460 | B2 | 6/2005 | DiStefano |
| 7,210,817 | B2 | 5/2007 | Lee et al. |
| 7,274,844 | B2 | 9/2007 | Walt et al. |
| 7,511,283 | B2 | 3/2009 | Chor |
| 8,197,087 | B2 | 6/2012 | Sobue et al. |
| 8,246,666 | B2 | 8/2012 | Pressler et al. |
| 8,372,128 | B2 | 2/2013 | Reuben |
| 8,387,405 | B2 | 3/2013 | Johnson |
| 8,556,950 | B2 | 10/2013 | Rioux et al. |
| 9,138,499 | B2 | 9/2015 | Bettles et al. |
| 9,592,374 | B2 | 3/2017 | Muse |
| 9,604,072 | B2 | 3/2017 | Brezinski |
| 9,925,285 | B1 | 3/2018 | Zaborsky et al. |
| 9,974,877 | B2 | 5/2018 | Bettles et al. |
| 9,981,052 | B2 | 5/2018 | Clynne et al. |
| 10,314,928 | B2 | 6/2019 | Dobrinsky et al. |
| 10,603,393 | B2 | 3/2020 | Rioux et al. |
| 10,610,609 | B2 | 4/2020 | Swaney et al. |
| 10,639,389 | B2 * | 5/2020 | Paul .......................... A61L 2/12 |
| 2002/0081228 | A1 | 6/2002 | Hui et al. |
| 2002/0168287 | A1 | 11/2002 | Eckhardt et al. |
| 2003/0018373 | A1 | 1/2003 | Eckhardt et al. |
| 2003/0036735 | A1 | 2/2003 | Jepson et al. |
| 2003/0063997 | A1 | 4/2003 | Fryer et al. |
| 2005/0101854 | A1 | 5/2005 | Larson et al. |
| 2007/0123825 | A1 | 5/2007 | King et al. |
| 2008/0027399 | A1 | 1/2008 | Harding et al. |
| 2008/0103560 | A1 | 5/2008 | Powell et al. |
| 2008/0257355 | A1 | 10/2008 | Rao et al. |
| 2008/0283769 | A1 | 11/2008 | Deshays |
| 2009/0177163 | A1 | 7/2009 | King et al. |
| 2010/0145721 | A1 | 6/2010 | Deshays |
| 2010/0296971 | A1 | 11/2010 | Gaska et al. |
| 2011/0144566 | A1 | 6/2011 | Dacey, Jr. et al. |
| 2012/0053512 | A1 | 3/2012 | Muse |
| 2012/0116294 | A1 | 5/2012 | Boenig et al. |
| 2012/0143138 | A1 | 6/2012 | King et al. |
| 2012/0161032 | A1 | 6/2012 | Arcand et al. |
| 2012/0321509 | A1 | 12/2012 | Bak |
| 2013/0303996 | A1 | 11/2013 | Rasooly et al. |
| 2013/0323119 | A1 | 12/2013 | Alwan |
| 2013/0323120 | A1 | 12/2013 | Ma |
| 2014/0217307 | A1 | 8/2014 | Messina et al. |
| 2014/0257186 | A1 | 9/2014 | Kerr |
| 2015/0080851 | A1 | 3/2015 | Kurth et al. |
| 2015/0148734 | A1 | 5/2015 | Fewkes et al. |
| 2015/0157209 | A1 | 6/2015 | Dantus |
| 2015/0165185 | A1 | 6/2015 | Cohen et al. |
| 2015/0217010 | A1 | 8/2015 | Whitney |
| 2015/0231287 | A1 | 8/2015 | Lin et al. |
| 2015/0238747 | A1 | 8/2015 | Russo |
| 2015/0245810 | A1 | 9/2015 | Shine et al. |
| 2015/0273093 | A1 | 10/2015 | Holub et al. |
| 2015/0283277 | A1 | 10/2015 | Schafer et al. |
| 2016/0038621 | A1 | 2/2016 | Mctor et al. |
| 2016/0128526 | A1 * | 5/2016 | Dobrinsky ........... A47K 13/302 4/233 |
| 2016/0151639 | A1 | 6/2016 | Scharf et al. |
| 2016/0303265 | A1 | 10/2016 | Coles |
| 2016/0310077 | A1 | 10/2016 | Hunter et al. |
| 2016/0317687 | A1 | 11/2016 | Dayton |
| 2017/0136209 | A1 | 5/2017 | Burnett et al. |
| 2017/0173251 | A1 | 6/2017 | Doyle et al. |
| 2017/0196478 | A1 | 7/2017 | Hunter |
| 2017/0216466 | A1 | 8/2017 | Dujowich et al. |
| 2017/0232123 | A1 | 8/2017 | Burapachaisri et al. |
| 2017/0252550 | A1 | 9/2017 | Wegener et al. |
| 2017/0281812 | A1 | 10/2017 | Dobrinsky et al. |
| 2017/0296142 | A1 | 10/2017 | Wodecki et al. |
| 2018/0280616 | A1 | 10/2018 | Witt et al. |
| 2018/0369560 | A1 | 12/2018 | Ball et al. |
| 2019/0111240 | A1 | 4/2019 | Fia et al. |
| 2019/0151587 | A1 | 5/2019 | Vazales et al. |
| 2019/0167825 | A1 | 6/2019 | Jones et al. |
| 2019/0192872 | A1 | 6/2019 | Schwarz et al. |
| 2019/0290360 | A1 | 9/2019 | Goodrich et al. |
| 2019/0290791 | A1 | 9/2019 | Baker et al. |
| 2019/0374668 | A1 | 12/2019 | Kopperschmidt et al. |
| 2020/0030473 | A1 | 1/2020 | Sugimoto et al. |
| 2020/0147248 | A1 | 5/2020 | Mintie et al. |
| 2020/0188543 | A1 | 6/2020 | Etter et al. |
| 2020/0254121 | A1 | 8/2020 | Swaney et al. |
| 2020/0261610 | A1 | 8/2020 | Rioux et al. |
| 2020/0324078 | A1 | 10/2020 | Motley et al. |
| 2020/0360549 | A1 * | 11/2020 | Neveu ........................ A61L 2/26 |
| 2020/0368379 | A1 | 11/2020 | Agarwal |
| 2021/0113725 | A1 | 4/2021 | Etter et al. |
| 2021/0154342 | A1 | 5/2021 | Canfield |
| 2021/0162081 | A1 * | 6/2021 | Zhang .................... G01N 21/94 |
| 2021/0204818 | A1 | 7/2021 | Akins et al. |
| 2021/0236859 | A1 | 8/2021 | Park et al. |
| 2021/0338879 | A1 | 11/2021 | Davis et al. |
| 2022/0016439 | A1 | 1/2022 | Shah et al. |
| 2022/0088250 | A1 | 3/2022 | Baarman |
| 2022/0096677 | A1 | 3/2022 | Chan et al. |
| 2022/0152243 | A1 | 5/2022 | Koppen et al. |
| 2022/0175983 | A1 | 6/2022 | Wood et al. |
| 2022/0203007 | A1 | 6/2022 | Yuds et al. |
| 2022/0273837 | A1 * | 9/2022 | Paul ........................ A61L 2/186 |
| 2022/0313851 | A1 | 10/2022 | Subramanya et al. |
| 2022/0347456 | A1 | 11/2022 | Messerly |
| 2022/0387643 | A1 | 12/2022 | Baarman |
| 2023/0089985 | A1 | 3/2023 | Li et al. |
| 2023/0118324 | A1 | 4/2023 | Hong et al. |
| 2023/0233716 | A1 | 7/2023 | Yoon et al. |
| 2023/0293741 | A1 | 9/2023 | Matsui et al. |
| 2023/0301626 | A1 | 9/2023 | Howell |
| 2024/0115749 | A1 | 4/2024 | Payne et al. |
| 2024/0188859 | A1 | 6/2024 | Fellner et al. |
| 2024/0189467 | A1 | 6/2024 | Urry et al. |
| 2024/0226350 | A1 | 7/2024 | Payne et al. |
| 2024/0226352 | A1 | 7/2024 | Fellner et al. |
| 2024/0252789 | A1 | 8/2024 | Hayden et al. |
| 2024/0335636 | A1 | 10/2024 | Laine et al. |
| 2024/0342325 | A1 | 10/2024 | Urry et al. |
| 2024/0350688 | A1 | 10/2024 | Prince |
| 2024/0374770 | A1 | 11/2024 | Durfee |
| 2025/0073360 | A1 | 3/2025 | Payne et al. |

FOREIGN PATENT DOCUMENTS

| | | | | |
|---|---|---|---|---|
| CN | 104873219 | A | 9/2015 | |
| CN | 106308727 | A | 1/2017 | |
| CN | 108430533 | A | 8/2018 | |
| CN | 208481489 | U | 2/2019 | |
| CN | 209790441 | U | 12/2019 | |
| CN | 213373944 | U | 6/2021 | |
| CN | 213551294 | U | 6/2021 | |
| CN | 113101207 | A | 7/2021 | |
| CN | 213642120 | U | 7/2021 | |
| CN | 113476076 | A | 10/2021 | |
| CN | 215426269 | U | 1/2022 | |
| EP | 3195805 | A1 | 7/2017 | |
| EP | 3738617 | A2 * | 11/2020 | ............... A61L 2/10 |
| JP | 2005198761 | A | 7/2005 | |
| KR | 20110050077 | A * | 5/2011 | ............... A61L 2/16 |
| KR | 20140003473 | U | 6/2014 | |
| KR | 101654328 | B1 | 9/2016 | |
| KR | 20220000634 | U | 3/2022 | |
| KR | 20220063891 | A | 5/2022 | |
| KR | 102452057 | B1 | 10/2022 | |
| WO | 9607451 | A2 | 3/1996 | |
| WO | 2011068545 | A1 | 6/2011 | |
| WO | 2011107540 | A1 | 9/2011 | |
| WO | 2013134421 | A1 | 9/2013 | |
| WO | 2014165854 | A1 | 10/2014 | |
| WO | 2015157518 | A1 | 10/2015 | |
| WO | 2019108431 | A1 | 6/2019 | |

(56) References Cited

FOREIGN PATENT DOCUMENTS

| | | | | | |
|---|---|---|---|---|---|
| WO | WO-2020115230 | A1 * | 6/2020 | ............... | A61L 2/10 |
| WO | 2020167843 | A1 | 8/2020 | | |
| WO | 2021146667 | A1 | 7/2021 | | |
| WO | 2021146701 | A1 | 7/2021 | | |
| WO | 2021157769 | A1 | 8/2021 | | |
| WO | 2022036886 | A1 | 2/2022 | | |
| WO | 2022046138 | A1 | 3/2022 | | |
| WO | 2022200038 | A2 | 9/2022 | | |
| WO | 2022232479 | A1 | 11/2022 | | |
| WO | 2023183426 | A1 | 9/2023 | | |
| WO | 2024081335 | A1 | 4/2024 | | |
| WO | 2024124112 | A1 | 6/2024 | | |
| WO | 2024129817 | A1 | 6/2024 | | |
| WO | 2024/151420 | A1 | 7/2024 | | |
| WO | 2024/151421 | A1 | 7/2024 | | |
| WO | 2024/151648 | A1 | 7/2024 | | |
| WO | 2024163670 | A1 | 8/2024 | | |
| WO | 2024211387 | A1 | 10/2024 | | |
| WO | 2024215932 | A1 | 10/2024 | | |
| WO | 2024220523 | A1 | 10/2024 | | |
| WO | 2024233805 | A1 | 11/2024 | | |
| WO | 2025049496 | A1 | 3/2025 | | |

OTHER PUBLICATIONS

PCT/US2023/083767 filed Dec. 13, 2023, International Search Report and Written Opinion dated Apr. 25, 2024.

PCT/US2023/085837 filed Dec. 22, 2023, International Search Report and Written Opinion dated Apr. 9, 2024.

PCT/US2024/010902 filed Jan. 9, 2024, International Search Report and Written Opinion dated Apr. 24, 2024.

Changtong et al., "A porphyrin molecule that generates, traps, stores, and releases singlet oxygen.", Journal of Photochemistry and Photobiology A: Chemistry 260 (Sep. 13, 2013).

PCT/US2022/026888 filed Apr. 29, 2022 International Search Report and Writtent Opinion dated Jul. 29, 2022.

Tsen et al., "Inactivation of multidrug-resistant bacteria and bacterial spores and generation of high-potency bacterial vaccines using ultrashort pulsed lasers." Journal of Biophotonics, 2021.

PCT/US2023/083089 filed Dec. 8, 2023, International Search Report and Written Opinion dated Jun. 3, 2024.

PCT/US2023/085839 filed Dec. 22, 2023, International Search Report and Written Opinion dated Jun. 11, 2024.

PCT/US2024/013858 filed Jan. 31, 2024, International Search Report and Written Opinion dated May 22, 2024.

Cabral, João, and Rodrigues A. G. "Blue light disinfection in hospital infection control: advantages, drawbacks, and pitfalls." Antibiotics 8.2 (2019): 58.

Changtong, Chuchawin, et al. "A porphyrin molecule that generates, traps, stores, and releases singlet oxygen." Journal of Photochemistry and Photobiology A: Chemistry 260 (2013): 9-13.

Halstead, Fenella D., et al. "The potential of visible blue light (405 nm) as a novel decontamination strategy for carbapenemase-producing enterobacteriaceae (CPE)." Antimicrobial Resistance & Infection Control 8.1 (2019): 1-8.

Tsen, Shaw-Wei David, et al. "Inactivation of multidrug-resistant bacteria and bacterial spores and generation of high-potency bacterial vaccines using ultrashort pulsed lasers." Journal of Biophotonics 15.2 (2022): e202100207.

PCT/US2024/044069 filed Aug. 27, 2024, International Search Report and Written Opinion dated Jan. 31, 2025.

U.S. Appl. No. 17/732,614, filed Apr. 29, 2022 Non-Final Office Action dated May 9, 2025.

U.S. Appl. No. 17/963,594, filed Oct. 11, 2022 Restriction Requirement dated Jun. 3, 2025.

U.S. Appl. No. 18/125,029, filed Mar. 22, 2023 Notice of Allowance dated Dec. 18, 2024.

PCT/US2024/024136 filed Apr. 11, 2024, International Search Report and Written Opinion dated Sep. 18, 2024.

PCT/US2024/024969 filed Apr. 17, 2024, International Search Report and Written Opinion dated Sep. 27, 2024.

PCT/US2024/028630 filed May 9, 2024, International Search Report and Written Opinion dated Sep. 18, 2024.

PCT/US2023/015961 filed Mar. 22, 2023, International Search Report and Written Opinion dated Jul. 17, 2023.

PCT/US2023/034981 filed Oct. 11, 2023, International Search Report and Written Opinion dated Dec. 11, 2023.

U.S. Appl. No. 17/732,614, filed Apr. 29, 2022 Non-Final Office Action dated Jan. 28, 2026.

U.S. Appl. No. 17/963,594, filed Oct. 11, 2022 Advisory Action dated Mar. 6, 2026.

U.S. Appl. No. 17/963,594, filed Oct. 11, 2022 Final Office Action dated Jan. 8, 2026.

U.S. Appl. No. 18/077,994, filed Dec. 8, 2022 Final Office Action dated Feb. 12, 2026.

U.S. Appl. No. 18/080,624, filed Dec. 13, 2022 Final Office Action dated Jan. 30, 2026.

U.S. Appl. No. 18/095,469, filed Jan. 10, 2023 Notice of Allowance dated Jan. 7, 2026.

U.S. Appl. No. 18/104,448, filed Feb. 1, 2023 Final Office Action dated Feb. 25, 2026.

U.S. Appl. No. 18/132,261, filed Apr. 7, 2023 Non-Final Office Action dated Feb. 9, 2026.

U.S. Appl. No. 18/136,111, filed Apr. 18, 2023 Notice of Allowance dated Dec. 23, 2025.

U.S. Appl. No. 18/239,048, filed Aug. 28, 2023 Restriction Requirement dated Mar. 3, 2026.

CS Medical "Caring for TEE Probes the Right Way" Mar. 17, 2022.

PCT/US2023/085837 filed Dec. 22, 2023, International Preliminary Report on Patentability dated Jul. 3, 2025.

PCT/US2024/013858 filed Jan. 31, 2024 International Preliminary Report on Patentability dated Jul. 31, 2025.

PCT/US2024/022801 filed Apr. 4, 2024, International Search Report and Written Opinion dated Sep. 6, 2024.

U.S. Appl. No. 17/732,614, filed Apr. 29, 2022 Advisory Action Nov. 14, 2025.

U.S. Appl. No. 17/732,614, filed Apr. 29, 2022 Final Office Action dated Sep. 4, 2025.

U.S. Appl. No. 17/963,594, filed Oct. 11, 2022 Non-Final Office Action dated Aug. 22, 2025.

U.S. Appl. No. 18/077,994, filed Dec. 8, 2022 Non-Final Office Action dated Jul. 30, 2025.

U.S. Appl. No. 18/080,624, filed Dec. 13, 2022 Non-Final Office Action dated Oct. 1, 2025.

U.S. Appl. No. 18/080,624, filed Dec. 13, 2022 Restriction Requirement dated Jul. 10, 2025.

U.S. Appl. No. 18/094,760, filed Jan. 9, 2023 Non-Final Office Action dated Sep. 10, 2025.

U.S. Appl. No. 18/094,760, filed Jan. 9, 2023 Restriction Requirement dated Jun. 18, 2025.

U.S. Appl. No. 18/095,469, filed Jan. 10, 2023 Non-Final Office Action dated Sep. 8, 2025.

U.S. Appl. No. 18/104,448, filed Feb. 1, 2023 Non-Final Office Action dated Oct. 30, 2025.

U.S. Appl. No. 18/132,261, filed Apr. 7, 2023 Restriction Requirement dated Nov. 10, 2025.

U.S. Appl. No. 18/195,018, filed May 9, 2023 Final Office Action dated Oct. 23, 2025.

U.S. Appl. No. 18/195,018, filed May 9, 2023 Non-Final Office Action dated Jul. 3, 2025.

U.S. Appl. No. 17/732,614, filed Apr. 29, 2022 Final Office Action dated Jun. 1, 2026.

U.S. Appl. No. 17/963,594, filed Oct. 11, 2022 Non-Final Office Action dated Apr. 27, 2026.

U.S. Appl. No. 18/077,994, filed Dec. 8, 2022 Advisory Action dated Apr. 23, 2026.

U.S. Appl. No. 18/077,994, filed Dec. 8, 2022 Non-Final Office Action dated Jun. 12, 2026.

U.S. Appl. No. 18/080,624, filed Dec. 13, 2022 Advisory Action dated Apr. 7, 2026.

U.S. Appl. No. 18/094,760, filed Jan. 9, 2023 Advisory Action dated May 21, 2026.

(56) References Cited

OTHER PUBLICATIONS

U.S. Appl. No. 18/094,760, filed Jan. 9, 2023 Final Office Action dated Mar. 19, 2026.
U.S. Appl. No. 18/104,448, filed Feb. 1, 2023 Advisory Action dated May 1, 2026.
U.S. Appl. No. 18/104,448, filed Feb. 1, 2023 Notice of Allowance dated Jun. 6, 2026.
U.S. Appl. No. 18/195,018, filed May 9, 2023 Non-Final Office Action dated Apr. 9, 2026.
U.S. Appl. No. 18/633,354, filed Apr. 11, 2024 Non-Final Office Action dated May 6, 2026.
U.S. Appl. No. 18/080,624, filed Dec. 13, 2022 Non-Final Office Action dated Aug. 7, 2026.
U.S. Appl. No. 18/094,760, filed Jan. 9, 2023 Non-Final Office Action dated Jul. 1, 2026.
U.S. Appl. No. 18/132,261, filed Apr. 7, 2023 Final Office Action dated Jul. 16, 2026.
U.S. Appl. No. 18/239,048, filed Aug. 28, 2023 Non-Final Office Action dated Jun. 18, 2026.

* cited by examiner

UV DISINFECTION SYSTEM AND METHODS

BACKGROUND

Ultraviolet ("UV") light is known to damage bacteria and their endotoxins, and such knowledge has been implemented in various disinfection systems. However, existing disinfection systems rely on either user knowledge of best practices for disinfecting various articles or generalized disinfection programs without regard to particular needs of the various articles. For example, certain polymeric articles might degrade if exposed to wavelengths in certain ranges if exposed to those wavelengths for too long. What is needed is a disinfection system that does not require user knowledge, thereby eliminating user error in disinfecting articles in need of disinfection. Further, a disinfection system is needed that can disinfect such articles with regard to their particular needs, thereby ensuring effective disinfection the articles while maintaining their integrity.

Disclosed herein are UV disinfection systems and methods that address the foregoing.

SUMMARY

Disclosed herein is a disinfection system for disinfecting medical devices. The disinfection system includes, in some embodiments, a console and a disinfection unit operably coupled to the console. The console has electronic circuitry including memory and one or more processors. The memory includes executable instructions configured to cause the console to perform various processes when executed by the one-or-more processors. The various processes include characterizing with medical-device characterization logic one or more characteristics of at least an elongate portion of a medical device for establishing or maintaining vascular access in a patient. The various processes also include determining with disinfection logic a disinfection profile for disinfecting at least the elongate portion of the medical device with UV light. The disinfection unit includes a disinfection compartment and a UV-light source disposed in the disinfection compartment. The disinfection compartment is suitably sized to enclose the medical device therein. The UV-light source is for disinfecting at least the elongate portion of the medical device with the UV light in accordance with the disinfection profile.

In some embodiments, the UV-light source is configured to emit UV light in a range from about 100 nm to about 280 nm.

In some embodiments, the UV-light source is a low-pressure mercury lamp, an excimer lamp, a pulsed xenon lamp, or one or more light-emitting diodes ("LEDs") disposed in the disinfection department.

In some embodiments, the disinfection system further includes a local database in the memory or access to a shared database of medical devices for establishing or maintaining vascular access in patients. The local or shared database relates the medical devices to medical-device characteristics for characterizing at least the elongate portion of the medical device with the medical-device characterization logic.

In some embodiments, the medical-device characteristics are selected from at least materials of the medical devices; properties of the materials; surface topographies, and expected contamination levels based on the materials.

In some embodiments, the disinfection system further includes one or more machine-readable data readers selected from a barcode reader, a radiofrequency identification ("RFID")-tag reader, a magnetic-ink character recognition ("MICR") reader, and an optical character recognition ("OCR") reader configured to read machine-readable data associated with the medical device for identifying the medical device in the local or shared database with the medical-device characterization logic.

In some embodiments, the disinfection profile includes a range of wavelengths or a peak wavelength for the UV light, an exposure time for the UV light, a power of the UV light, or a combination thereof.

In some embodiments, the disinfection system further includes an ultrasound probe. The ultrasound probe is configured to emit ultrasound signals into a limb of a patient and receive echoed ultrasound signals from the patient's limb by way of a piezoelectric sensor array. The various processes performed by the console also including transforming the echoed ultrasound signals to produce ultrasound images.

In some embodiments, the disinfection compartment is further suitably sized to enclose the ultrasound probe therein for disinfection of the ultrasound probe between uses thereof.

In some embodiments, the disinfection system further includes a display integrated into the console or a monitor operably connected to the console. The various processes performed by the console further including sending display signals to the display for displaying disinfection-related information selected from at least medical-device identification, disinfection state, and a disinfection-progress indicator.

Also disclosed herein is a method of a disinfection system for disinfecting medical devices. The method includes, in some embodiments, an instantiating step of instantiating various processes upon one or more processors of a console of the system executing instructions in memory of the console. The various processes include a medical device-characterizing process for characterizing with medical-device characterization logic one or more characteristics of at least an elongate portion of a medical device for establishing or maintaining vascular access in a patient. The various processes also include a disinfection profile-determining process for determining with disinfection logic a disinfection profile for disinfecting at least the elongate portion of the medical device with UV light. The various processes also include a disinfecting process for disinfecting at least the elongate portion of the medical device in accordance with the disinfection profile using a UV-light source disposed in a disinfection compartment of a disinfection unit operably coupled to the console.

In some embodiments, the UV-light source is configured to emit UV light in a range from about 100 nm to about 280 nm.

In some embodiments, the UV-light source is a low-pressure mercury lamp, an excimer lamp, a pulsed xenon lamp, or one or more LEDs disposed in the disinfection department.

In some embodiments, the various processes also include a database-accessing process for accessing a local database in the memory or a shared database of medical devices for establishing or maintaining vascular access in patients. The local or shared database relates the medical devices to medical-device characteristics for characterizing at least the elongate portion of the medical device with the medical-device characterization logic.

In some embodiments, the medical-device characteristics are selected from at least materials of the medical devices; properties of the materials; surface topographies, and expected contamination levels based on the materials.

In some embodiments, the various processes also include a machine-readable-data-reading process and a medical device-identifying process. The machine-readable-data-reading process reads in machine-readable data associated with the medical device using one or more machine-readable data readers selected from a barcode reader, an RFID-tag reader, an MICR reader, and an OCR reader. The medical device-identifying process identifies the medical device in the local or shared database with the medical-device characterization logic.

In some embodiments, the disinfection profile includes a range of wavelengths or a peak wavelength for the UV light, an exposure time for the UV light, a power of the UV light, or a combination thereof.

In some embodiments, the various processes also include an ultrasound signal-processing process. The ultrasound signal-processing process transforms echoed ultrasound signals to produce ultrasound images. The echoed ultrasound signals are received from a patient's limb by a piezoelectric sensor array of an ultrasound probe upon emitting ultrasound signals into the limb of the patient.

In some embodiments, the disinfection compartment is further suitably sized to enclose the ultrasound probe therein for disinfection of the ultrasound probe between uses thereof.

In some embodiments, the various processes also include a display process. The display process displays disinfection-related information on a display integrated into the console or a monitor operably connected to the console. The disinfection-related information is selected from at least medical-device identification, disinfection state, and a disinfection-progress indicator.

These and other features of the concepts provided herein will become more apparent to those of skill in the art in view of the accompanying drawings and following description, which describe particular embodiments of such concepts in greater detail.

DRAWINGS

FIG. 1 provides a disinfection system in accordance with some embodiments.

Figure 2:
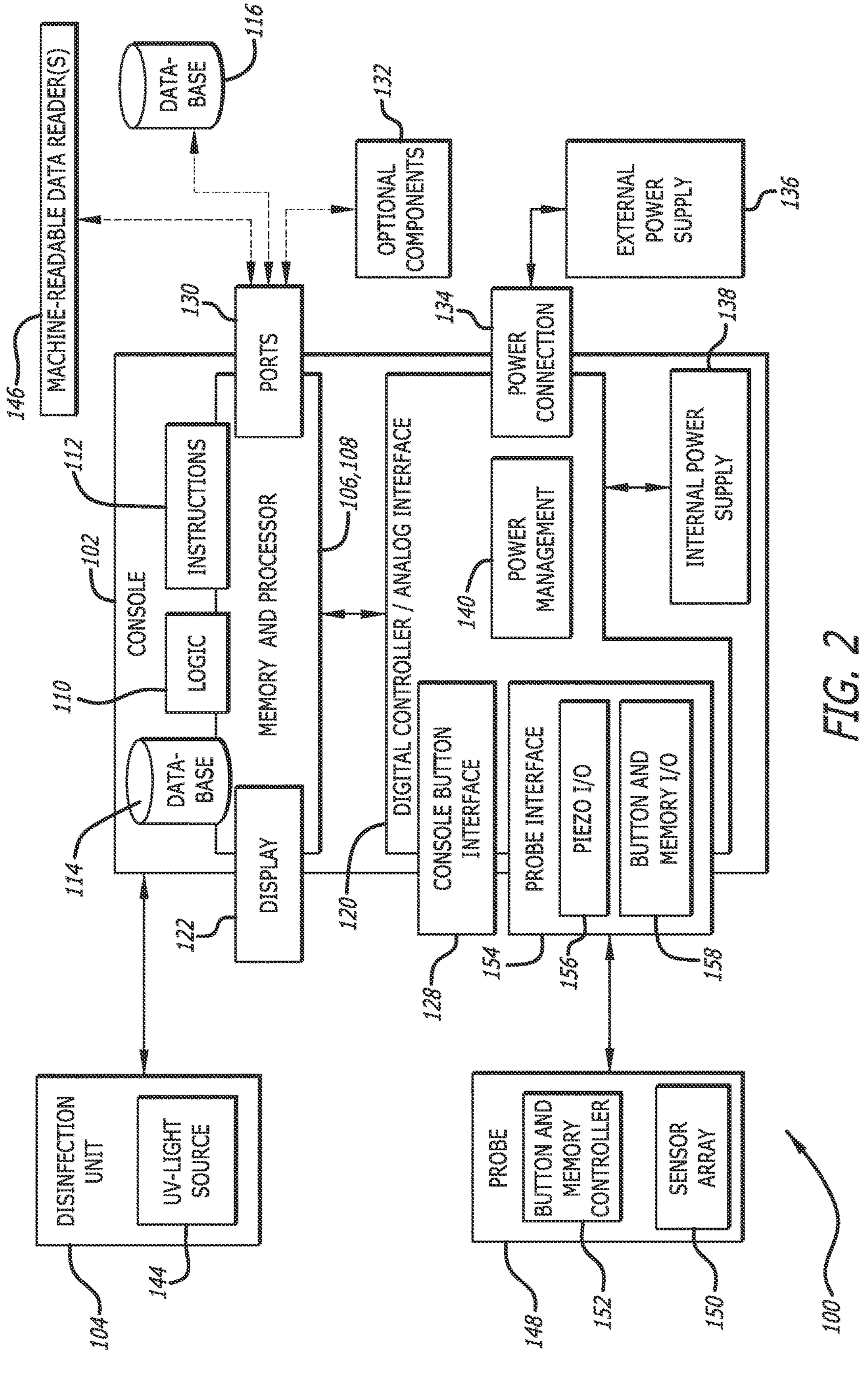

FIG. 2 provides a block diagram of the disinfection system in accordance with some embodiments.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. In addition, any of the foregoing features or steps can, in turn, further include one or more features or steps unless indicated otherwise. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

"Proximal" is used to indicate a portion, section, piece, element, or the like of a medical device intended to be near or relatively nearer to a clinician when the medical device is used on a patient. For example, a "proximal portion" or "proximal section" of the medical device includes a portion or section of the medical device intended to be near the clinician when the medical device is used on the patient. Likewise, a "proximal length" of the medical device includes a length of the medical device intended to be near the clinician when the medical device is used on the patient. A "proximal end" of the medical device is an end of the medical device intended to be near the clinician when the medical device is used on the patient. The proximal portion, the proximal section, or the proximal length of the medical device need not include the proximal end of the medical device. Indeed, the proximal portion, the proximal section, or the proximal length of the medical device can be short of the proximal end of the medical device. However, the proximal portion, the proximal section, or the proximal length of the medical device can include the proximal end of the medical device. Should context not suggest the proximal portion, the proximal section, or the proximal length of the medical device includes the proximal end of the medical device, or if it is deemed expedient in the following description, "proximal portion," "proximal section," or "proximal length" can be modified to indicate such a portion, section, or length includes an end portion, an end section, or an end length of the medical device for a "proximal end portion," a "proximal end section," or a "proximal end length" of the medical device, respectively.

"Distal" is used to indicate a portion, section, piece, element, or the like of a medical device intended to be near, relatively nearer, or even in a patient when the medical device is used on the patient. For example, a "distal portion" or "distal section" of the medical device includes a portion or section of the medical device intended to be near, relatively nearer, or even in the patient when the medical device is used on the patient. Likewise, a "distal length" of the medical device includes a length of the medical device intended to be near, relatively nearer, or even in the patient when the medical device is used on the patient. A "distal end" of the medical device is an end of the medical device intended to be near, relatively nearer, or even in the patient when the medical device is used on the patient. The distal portion, the distal section, or the distal length of the medical device need not include the distal end of the medical device. Indeed, the distal portion, the distal section, or the distal length of the medical device can be short of the distal end of the medical device. However, the distal portion, the distal section, or the distal length of the medical device can include the distal end of the medical device. Should context not suggest the distal portion, the distal section, or the distal length of the medical device includes the distal end of the medical device, or if it is deemed expedient in the following description, "distal portion," "distal section," or "distal length" can be modified to indicate such a portion, section, or length includes an end portion, an end section, or an end length of the medical device for a "distal end portion," a "distal end section," or a "distal end length" of the medical device, respectively.

Unless defined otherwise, all technical and scientific terms used herein have the same meaning as commonly understood by those of ordinary skill in the art.

Again, UV light is known to damage bacteria and their endotoxins, and such knowledge has been implemented in various disinfection systems. However, existing disinfection systems rely on either user knowledge of best practices for disinfecting various articles or generalized disinfection programs without regard to particular needs of the various articles. For example, certain polymeric articles might degrade if exposed to wavelengths in certain ranges if exposed to those wavelengths for too long. What is needed is a disinfection system that does not require user knowledge, thereby eliminating user error in disinfecting articles in need of disinfection. Further, a disinfection system is needed that can disinfect such articles with regard to their particular needs, thereby ensuring effective disinfection the articles while maintaining their integrity.

Disclosed herein are UV disinfection systems and methods that address the foregoing. Indeed, as will become more apparent to those of skill in the art in view of the accompanying drawings and following description, the UV disinfection systems can, in real-time, characterize medical devices and determine disinfection profiles therefor in accordance with their materials and properties of those materials, surface topographies, and expected contamination levels of the medical devices. Such characterization of medical devices and the disinfection profiles obviates any user input in accordance with his or her knowledge or source of disinfection information, which, in turn, obviates any user error. Further, the characterization of medical devices and the disinfection profiles therefor ensure effective disinfection of the medical devices while minimizing UV-light exposure to maintain integrity of the medical devices.

FIGS. 1 and 2 illustrate a disinfection system 100 for disinfecting medical devices with at least UV light in accordance with some embodiments.

As shown, the disinfection system 100 can include a console 102 and a disinfection unit 104 operably coupled to the console 102; however, it should be understood the disinfection system 100 can be integrated into a single, standalone disinfection unit with or without any of the additional components set forth below. As such, description for the console 102, the disinfection unit 104, or any of the additional components of the disinfection system 100 set forth below should be understood to apply to such a single, standalone disinfection unit as well. Indeed, the single, standalone disinfection unit can have the console 102 and the display 122 integrated into a top, back, or side of the disinfection unit 104 along with the ports 130 for connecting any of the additional components set forth below.

The console 102 can include electronic circuitry including memory 106, one or more processors 108, and logic 110. The one-or-more processors 108 and the memory 106 (e.g., primary memory such as non-volatile memory including electrically erasable, programmable, read-only memory ["EEPROM"] and volatile memory including static or dynamic random-access memory ["SRAM"] or ["DRAM"]) of the console 102 can be configured for controlling various functions of the disinfection system 100. Indeed, the memory 106 can include executable instructions 112 configured to cause the console 102 to perform various processes when executed by the one-or-more processors 108 such as the various processes set forth below. In addition, the memory 106 (e.g., secondary memory such as non-volatile memory of an internal storage device of the console 102) can include a local database 114 of medical devices for establishing or maintaining vascular access in patients. While not shown, the console 102 can also include one or more communications modules for wired or wireless access to a shared database 116 of the foregoing medical devices in addition to the local database 114 or as an alternative thereto. Such a local or shared database 114 or 116, which can be periodically updated, can relate the medical devices to medical-device characteristics for characterizing at least the elongate portion of the medical device 118 with the medical-device characterization logic.

The various processes can include, but are not limited to, characterizing with medical-device characterization logic of the logic 110 one or more characteristics of at least an elongate portion of a medical device 118 (e.g., a distal end portion of a catheter such as a peripherally inserted central catheter ["PICC"], a central venous catheter ["CVC"], or the like) for establishing or maintaining vascular access in a patient. The medical-device characterization logic can be configured to use machine-read data obtained by the one-or-more machine-readable data readers 146 to search the local or shared database 114 or 116 for characterizing the medical device 118 with the medical-device characteristics thereof found in the local or shared database 114 or 116. Notably, the medical-device characteristics in the local or shared database 114 or 116 can be selected from at least materials of the medical devices; properties of the materials including densities, porosities, absorbances or transmittances, reflectivities, opacities, photosensitivities, or the like; surface topographies of elongate portions of the medical devices including lays, roughnesses, wavinesses, or the like; and expected contamination levels of the medical devices based on the materials, packaging, storage conditions, or the like.

The various processes can also include determining with disinfection logic of the logic 110 a disinfection profile for disinfecting at least the elongate portion of the medical device 118 with the UV light. The disinfection profile can include a range of wavelengths or a peak wavelength for the UV light, an exposure time for exposure to the UV light, a power of the UV light, or a combination thereof. Notably, the power of the UV light need not be constant. Indeed, the power can ramp up from zero (i.e., 0 W) or a low power to a high power, oscillate between the zero or low power and the high power, or the like.

The various processes can also include sending display signals to the display 122 for displaying disinfection-related information selected from at least the medical-device identification 124, the disinfection state (e.g., disinfected or not disinfected), and the disinfection-progress indicator 126.

The various processes performed by the console 102 can also include emitting ultrasound signals into a patient with the ultrasound probe 148, when present, and transforming echoed ultrasound signals received from the patient to produce ultrasound images.

The console 102 can also include a digital controller or analog interface 120, which can be in communication with the one-or-more processors 108 and any of the additional components set forth below to govern interfacing between the console 102 and the disinfection unit 104, the one-or-more machine-readable data readers 146, if not integrated into the console 102, the ultrasound probe 148, if present, or any other components of the additional components set forth below.

The console 102 can also include a display 122 having a display screen such as a liquid crystal display ("LCD") screen integrated into the console 102 for displaying information to a clinician before, during, or after a disinfection process, an ultrasound procedure, etc. Alternatively, the display 122 can be separate from the console 102 such as part of an external monitor that can be operably connected to the console 102. Regardless, the display 122 can be configured to display disinfection-related information selected from at least a medical-device identification 124, a disinfection state (e.g., disinfected or not disinfected), and a disinfection-progress indicator 126. In addition, the display 122 can be configured to display one or more ultrasound images attained by the ultrasound probe 148.

The console 102 can also include a console button interface 128. In combination with control buttons on disinfection unit 104, the ultrasound probe 148, or any other components of the additional components set forth below, the console button interface 128 can be used by a clinician to immediately call up a desired mode (e.g., disinfection mode, ultrasound mode, etc.) of the disinfection system 100 on the display 122 for use by the clinician.

The console 102 can also include ports 130 for connecting any additional components of the disinfection system 100 including the one-or-more machine-readable data readers 146, if not integrated into the console 102 or disinfection unit 104, the ultrasound probe 148, or other optional components 132 such as a printer, a storage device, a keyboard, a mouse, etc. The ports 130 can be universal serial bus ("USB") ports, though other ports or a combination of various ports can be used.

The console 102 can also include a power connection 134 for connecting an external power supply 136. An internal power supply 138 (e.g., a disposable or rechargeable battery) can also be employed, either with the external power supply 136 or exclusive of the external power supply 136. The console 102 can also include power management circuitry 140 such as part of the digital controller or analog interface 120 of the console 102 to regulate power use and distribution.

The disinfection unit 104 can include a disinfection compartment 142 and a UV-light source 144 disposed in the disinfection compartment 142. The disinfection compartment 142 can be suitably sized to enclose the medical device 118 therein. Further, the disinfection compartment 142 can be suitably sized to enclose the ultrasound probe 148 therein for disinfection of the ultrasound probe 148 between uses thereof. The UV-light source 144 can be configured for disinfecting at least the elongate portion of the medical device 118 with the UV light in accordance with the disinfection profile. Notably, the UV-light source 144 can be configured to emit the UV light in a range from about 100 nm to about 280 nm, which corresponds to the so-called UVC range; however, the UV-light source 144 need not be limited to the UVC range. Indeed, the UV-light source 144 can be configured to emit UV light anywhere in the UV portion of the electromagnetic spectrum. In an example, the UV-light source 144 can be alternatively configured to emit the UV light in a range from about 280 nm to about 315 nm, which corresponds to the so-called UVB range. In another example, the UV-light source 144 can be alternatively configured to emit the UV light in a range from about 315 nm to about 400 nm, which corresponds to the so-called UVA range. In consideration of the UV-light source 144 being configured to emit the UV light in the UVC range, the UV-light source 144 can be a low-pressure mercury lamp with an emission peak at, for example, 254 nm; an excimer lamp with an emission peak at, for example, 222 nm; a pulsed xenon lamp, or one or more LEDs, which LEDs can have independently have emission peaks at, for example, 265, 273, or 280 nm.

The disinfection system 100 can also include one or more machine-readable data readers 146 selected from at least a barcode reader, an RFID-tag reader, an MICR reader, and an OCR reader configured to read machine-readable data associated with the medical device 118 such as make, model or type, lot, or the like for identifying the medical device 118 in the local or shared database 114 or 116 with the medical-device characterization logic.

The disinfection system 100 can also include an ultrasound probe 148. The ultrasound probe 148 can be configured to emit ultrasound signals into, for example, a limb of a patient and receive echoed ultrasound signals from the patient's limb by way of, for example, a piezoelectric sensor array 150. The ultrasound probe 148 can be configured with a continuous wave or a pulsed-wave imaging mode. For example, the ultrasound probe 148 can be configured with a pulsed-wave Doppler imaging mode for emitting and receiving the ultrasound signals.

The ultrasound probe 148 can include a button-and-memory controller 152 for governing operation of the ultrasound probe 148 and buttons thereof. The button-and-memory controller 152 can include non-volatile memory such as EEPROM. The button-and-memory controller 152 can be in operable communication with an ultrasound probe interface 154 of the console 102, which ultrasound probe 148 interface includes a piezoelectric input-output ("I/O") component 156 for interfacing with the piezoelectric sensor array 150 of the ultrasound probe 148 and a button-and-memory I/O component 158 for interfacing with the button-and-memory controller 152 of the ultrasound probe 148.

METHODS

Methods of the disinfection system 100 can include methods of using the disinfection system 100 to disinfect medical devices or methods of the disinfection system 100, itself, for disinfecting the medical devices. For example, a method of the disinfection system 100 for disinfecting the medical devices can include an instantiating step of instantiating various processes related to disinfecting the medical devices upon the one-or-more processors 108 of the console 102 executing the instructions 112 in the memory 106 of the console 102.

The various processes can include a medical device-characterizing process for characterizing with the medical-device characterization logic one or more characteristics of at least an elongate portion of a medical device (e.g., the elongate portion of the medical device 118) for establishing or maintaining vascular access in a patient.

The various processes can also include a disinfection profile-determining process for determining with the disinfection logic a disinfection profile for disinfecting at least the elongate portion of the medical device 118 with UV light. Again, the disinfection profile can include a range of wavelengths or a peak wavelength for the UV light, an exposure time for the UV light, a power of the UV light, or the combination thereof.

The various processes can also include a disinfecting process for disinfecting at least the elongate portion of the medical device 118 in accordance with the disinfection profile using the UV-light source 144 disposed in the disinfection compartment 142 of the disinfection unit 104 operably coupled to the console 102. Again, the UV-light source 144 can be a low-pressure mercury lamp, an excimer lamp, a pulsed xenon lamp, or one or more LEDs disposed in the disinfection department configured to emit the UV light in the 100- to 280-nm range of wavelengths.

The various processes can also include a database-accessing process for accessing the local database 114 in the memory 106 or the shared database 116 of medical devices for establishing or maintaining vascular access in patients. Again, the local or shared database 114 or 116 can relate the medical devices to the medical-device characteristics thereof for characterizing at least the elongate portion of the medical device 118 with the medical-device characterization logic. As set forth above, the medical-device characteristics are selected from at least the materials of the medical devices; the properties of the materials; the surface topographies, and the expected contamination levels based on the materials, packaging, storage conditions, or the like.

The various processes can also include a machine-readable-data-reading process and a medical device-identifying process. The machine-readable-data-reading process can read in machine-readable data associated with the medical device 118 using the one-or-more machine-readable data readers 146 selected from at least the barcode reader, the RFID-tag reader, the MICR reader, and the OCR reader. The medical device-identifying process can identify the medical device 118 in the local or shared database 114 or 116 with the medical-device characterization logic.

The various processes can also include an ultrasound signal-processing process. The ultrasound signal-processing process can transform echoed ultrasound signals to produce ultrasound images. The echoed ultrasound signals can be received from a patient's limb by a piezoelectric sensor array 150 of the ultrasound probe 148 upon emitting ultrasound signals into the limb of the patient.

The various processes can also include a display process. The display process can display disinfection-related information on the display 122 integrated into the console 102 or the monitor operably connected to the console 102. The disinfection-related information is selected from at least the medical-device identification 124, the disinfection state, and the disinfection-progress indicator 126.

While some particular embodiments have been disclosed herein, and while the particular embodiments have been disclosed in some detail, it is not the intention for the particular embodiments to limit the scope of the concepts provided herein. Additional adaptations or modifications can appear to those of ordinary skill in the art, and, in broader aspects, these adaptations or modifications are encompassed as well. Accordingly, departures may be made from the particular embodiments disclosed herein without departing from the scope of the concepts provided herein.

What is claimed is:

1. A disinfection system for disinfecting a medical device, the disinfection system comprising:

a local database or a shared database of medical devices for establishing or maintaining vascular access in patients, the local database or the shared database relating the medical devices to medical device characteristics;

one or more machine readable data readers configured to read machine readable data associated with the medical device for identifying the medical device in the local database or the shared database;

a console having electronic circuitry including memory and one or more processors, the memory including executable instructions configured to cause the console to perform various processes when executed by the one or more processors including:

reading the machine readable data associated with the medical device;

accessing the local database or the shared database of medical devices;

identifying the medical device in the local database or the shared database of medical devices based on the machine readable data associated with the medical device;

characterizing at least an elongate portion of the medical device based on the medical device characteristics from the local database or the shared database associated with the medical device, wherein the medical device characteristics include at least a material of the medical device;

determining a disinfection profile for disinfecting at least the elongate portion of the medical device with ultraviolet ("UV") light, wherein the disinfection profile is based on at least the material of the medical device; and disinfecting at least the elongate portion of the medical device in accordance with the disinfection profile; and a disinfection unit operably coupled to the console, the disinfection unit including:

a disinfection compartment suitably sized to enclose the medical device therein; and a UV light source disposed in the disinfection compartment for disinfecting at least the elongate portion of the medical device; and an ultrasound probe configured to emit ultrasound signals into a limb of a patient and receive echoed ultrasound signals from the limb of the patient by way of a piezoelectric sensor array, the various processes performed by the console further including transforming the echoed ultrasound signals to produce ultrasound images.

2. The disinfection system of claim 1, wherein the UV light source is configured to emit UV light in a range from about 100 nm to about 280 nm.

3. The disinfection system of claim 2, wherein the UV light source is a low-pressure mercury lamp, an excimer lamp, a pulsed xenon lamp, or one or more light-emitting diodes ("LEDs") disposed in the disinfection compartment.

4. The disinfection system of claim 1, wherein the medical device characteristics further include properties of the material of the medical device; surface topographies of the medical device, and expected contamination level based on the material of the medical device.

5. The disinfection system of claim 1, wherein the one or more machine readable data readers are selected from a barcode reader, a radiofrequency identification ("RFID")-tag reader, a magnetic-ink character recognition ("MICR") reader, and an optical character recognition ("OCR") reader.

6. The disinfection system of claim 1, wherein the disinfection profile includes a range of wavelengths or a peak wavelength for the UV light, an exposure time for the UV light, a power of the UV light, or a combination thereof.

7. The disinfection system of claim 1, wherein the disinfection compartment is further suitably sized to enclose the ultrasound probe therein for disinfection of the ultrasound probe between uses thereof.

8. The disinfection system of claim 1, further comprising:

a display integrated into the console or a monitor operably connected to the console, the various processes performed by the console further including sending display signals to the display for displaying disinfection related information selected from at least medical device identification, a disinfection state, and a disinfection progress indicator.

* * * * *